(12) United States Patent
Saura Lopez et al.

(10) Patent No.: US 9,345,795 B2
(45) Date of Patent: May 24, 2016

(54) APPARATUS FOR INSTANTANEOUS EXPANSION WITH VACUUM AND ULTRASOUND WAVES

(71) Applicant: Universidad Miguel Hernandez, Elche (ES)

(72) Inventors: Domingo Saura Lopez, Murcia (ES);
Nuria Marti Bruna, Murcia (ES);
Manuel Valero Roche, Orihuela (ES);
Eulalio Bernal Belda, Orihuela (ES);
Salud Vegara Gómez, Redovan (ES);
María de los Remedios Berenguer Martínez, Orihuela (ES); Vicente Micol Molina, Elche (ES)

(73) Assignee: UNIVERSIDAD MIGUEL HERNANDEZ (ES)

( * ) Notice: Subject to any disclaimer, the term of this patent is extended or adjusted under 35 U.S.C. 154(b) by 0 days.

(21) Appl. No.: 14/616,358

(22) Filed: Feb. 6, 2015

(65) Prior Publication Data

US 2015/0258225 A1 Sep. 17, 2015

Related U.S. Application Data

(63) Continuation of application No. PCT/ES2013/000191, filed on Aug. 8, 2013.

(30) Foreign Application Priority Data

Aug. 9, 2012 (ES) .................................. 201200830

(51) Int. Cl.
*A61L 2/00* (2006.01)
*B01J 19/30* (2006.01)
*A61L 2/025* (2006.01)
*A23L 3/30* (2006.01)
*A23L 3/015* (2006.01)
*A61L 2/02* (2006.01)

(52) U.S. Cl.
CPC ............... *A61L 2/025* (2013.01); *A23L 3/0155* (2013.01); *A23L 3/30* (2013.01); *A61L 2/02* (2013.01); *A23V 2002/00* (2013.01)

(58) Field of Classification Search
CPC ........ A23C 3/073; A23L 3/0155; A23L 3/16;
A23L 3/30; A23L 2/025; B67C 7/0073
USPC .................................. 422/1, 38–39, 198, 308
See application file for complete search history.

(56) References Cited

U.S. PATENT DOCUMENTS

| 3,293,046 A | 12/1966 | Werther |
| 5,026,564 A * | 6/1991 | Hayden .................. A23C 3/073 422/20 |
| 2009/0044700 A1 | 2/2009 | Dietlin et al. |

FOREIGN PATENT DOCUMENTS

| EP | 0727948 B1 | 7/1998 |
| ES | 2046944 A1 | 2/1994 |
| ES | 2118533 T3 | 9/1998 |
| WO | 02096530 A2 | 12/2002 |
| WO | 2006024762 A1 | 3/2006 |
| WO | 2011143731 A1 | 11/2011 |

OTHER PUBLICATIONS

International Search Report Application No. PCT/ES2013/000191 Completed: Dec. 17, 2013; Mailing Date: Dec. 17, 2013 2 pages.

* cited by examiner

*Primary Examiner* — Monzer R Chorbaji
(74) *Attorney, Agent, or Firm* — St Onge Steward Johston and Reens LLC

(57) ABSTRACT

This invention is based on forming an apparatus in which the technologies of flash vacuum expansion and simultaneous treatment with ultrasounds are combined for various applications in the food, pharmaceutical and cosmetics industries.

17 Claims, 4 Drawing Sheets

Figure 1:
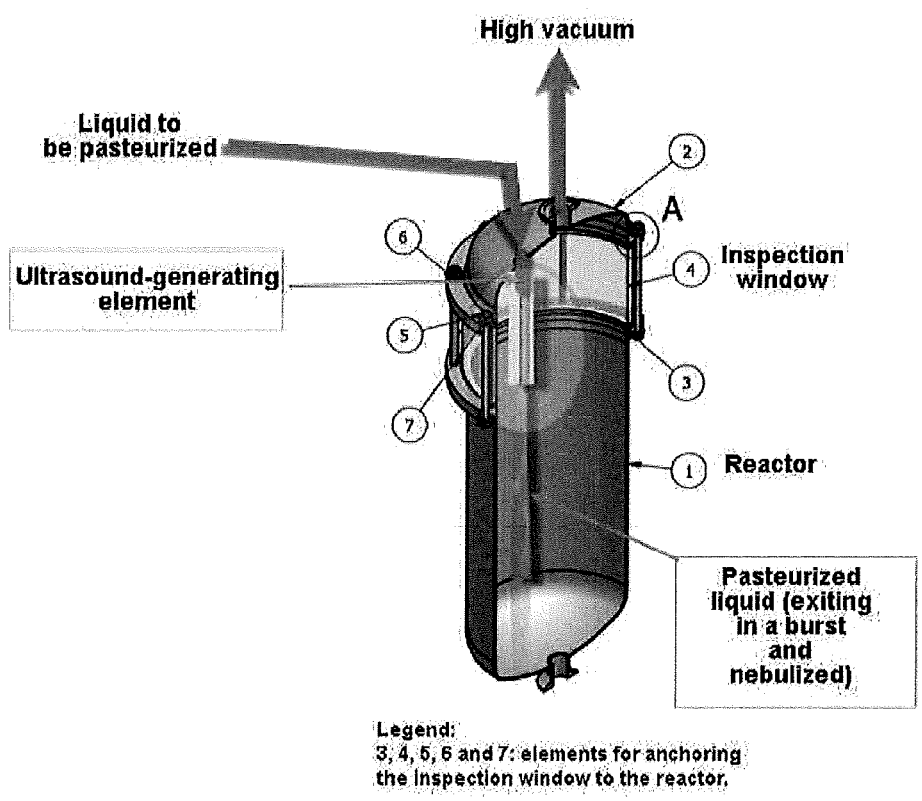

Legend:
3, 4, 5, 6 and 7: elements for anchoring the inspection window to the reactor.

APPARATUS FOR INSTANTANEOUS EXPANSION WITH VACUUM AND ULTRASOUND WAVES

FIELD OF THE INVENTION

The technical field of the present invention relates to apparatus intended for the preservation of foods, the production of new foods and/or functional foods, the production of nutraceuticals and extracts, the production of essences and aromas, the production of drugs, the production of cosmetics and the improvement in industrial output.

BACKGROUND OF THE INVENTION

The food, pharmaceutical and cosmetics industries have focused their efforts on searching for new economically viable production processes with moderate thermal treatments. Examples of these new production processes are the use of emerging technologies, such as the application of high pressure and the application of ultrasounds, and, in turn, the use of each of these two technologies combined with thermal treatments. On the other hand, flash vacuum expansion is a process in which the materials are heated with steam and are then immediately introduced in a vacuum chamber where they expand and break down, producing flash evaporation of a portion of the water contained in plant tissues and aromatic volatile components.

This invention is based on forming an apparatus in which the technologies of flash vacuum expansion and simultaneous treatment with ultrasounds are combined for various applications in the food, pharmaceutical and cosmetics industries.

In recent years the food, pharmaceutical and cosmetics industries have focused their efforts on searching for new economically viable production processes for the purpose of meeting constant consumer demand for novel, safe and non-perishable products (Señorans et al., 2003). Examples of these new production processes are the use of emerging technologies, such as the application of high pressure and the application of ultrasounds, and in turn, the use of each of these two technologies combined with moderate thermal treatments (Earnshaw 1996; Butz, Fernández García et al., 2003; Knorr et al., 2004; Urrutia-Benet et al., 2004; Ashokkumar et al., 2008).

Flash vacuum expansion is a process in which plant materials are heated at 60-90° C. with steam and are then immediately introduced in a vacuum chamber ($2.10^{-3}$ to $1.10^{-2}$ MPa) where they expand and break down due to the formation of microchannels within the tissues. Flash evaporation of a portion of the water contained in the constitutive plant tissues and aromatic volatile components takes place in this process. This evaporation process in turn produces cooling in the plant tissue, which produces a structural disruption, and accordingly accelerates the phenomenon of diffusion or maceration of the components thereof (Brat, 2001).

Different pieces of equipment have developed technologies in which flash vacuum expansion is applied.

Patent document WO2006/024762 A1 discloses a process of cooling at reduced pressure including the installation for implementing same. The method consists of an installation for cooling plants from temperature T1 to a lower temperature T3, in which the plants at temperature T1 are subjected to reduced pressure to partially vaporize the water contained therein and to cool said plants to temperature T3. Fractional cooling takes place: a first step cools the plants from temperature T1 to intermediate temperature T2, carrying out a first vaporization in a first cooling chamber under absolute reduced pressure P1; a second step consisting of cooling said plants from temperature T2 to T3, involving a second vaporization in a second cooling chamber under absolute reduced pressure P2, and said plants end up at temperature T3 which is less than 30° C. and preferably less than 28° C. after the second cooling step (Merican, 2006)

Another system for cooling a hot juice by partial, low-pressure evaporation is disclosed in patent document WO 02/096530 A2. A hot juice is subjected to several pressure reductions in at least two different compartments which communicate with each another by means of a pulsed-effect valve. The juice is subjected to two different pressure reductions in said compartments, each compartment being communicated with a condenser which condenses the vapor produced by the pressure reduction. The serially or parallel mounted condensers are connected to a vacuum pump by means of a control valve which can permanently adjust the pressure in each condenser to a value which is lower than the saturated vapor pressure corresponding to the temperature of the generated vapor. The invention is characterized in that the compartments are superposed and communicate with each other therein by means of an opening through which the juice passes, said position being open or closed either fully or partially by a variably positioned shutter element, creating a pulsed effect to remove the solid particles contained in the juice. (Nadeau, 2002).

French patent document 2813010 discloses a process for manufacturing a pectin-rich citric extract using the low-pressure method as follows: the flavedo is removed by means of scraping, the fruit is heated at a temperature of less than 110° C., and the hot citrus is subjected to reduced pressure for less than 3 seconds. A pulp-rich product that can be used to obtain soluble pectin-rich extract is finally obtained.

Patent document EP0727948 (A1) relates to processing hydrated plant materials, specifically for the extraction of juice and flavor from various substrates such as fruit, vegetables or leaves. It specifically relates to an installation in which it is unnecessary to add exogenous water to heat or bleach said materials. It is a continuously operating installation consisting of a heating chamber, a decompression and vaporization chamber connected to the heating chamber and to a condenser which is in turn connected to a vacuum pump (Cogat, 1996).

This technology is based on the developments described in patent document U.S. Pat. No. 3,293,046 of Werther (1966), French patent document 263833 of Cogat, Hunez and Pieribattesti (1988), and French patent document 2656547 of Cogat (1989).

This technology has given rise to multiple applications. The applications of flash expansion technology are specifically described below.

Flash vacuum expansion has been used in obtaining volatile compounds from passion fruit purée. The vapor heating process provides a purée with a higher concentration of total volatile compounds, particularly esters, compared to a reference purée due to the incorporation in the purée of part of the peel. After expansion in a vacuum, the purée is depleted of volatile components due to the flash evaporation of water when the fruits are introduced in the vacuum chamber. Most of these volatile compounds are recovered in the aromatic liquors generated by going through the expansion vacuum, and these could be added to the purée (Brat et al., 2000). Also by means of applying flash expansion to a purple passion fruit purée an intermediate product is obtained that is somewhere between a juice and a purée, giving rise to a new food product, with an output that exceeds that of the process for conventionally obtaining such products by two-fold. The high viscosity of the mash is closely related to its content of starch-free alcohol-insoluble residues (Brat, 2001).

Compared to conventional techniques, the method of treating grapes before wine fermentation by means of flash expansion technology provided a pronounced increase in the amount of pigments. The amount of total phenols can be 50% greater than that found in control wines. This increase in the polyphenol content is stable for years. Total dry weight increased up to a maximum of 30 g/L. The wines thus produced are less susceptible to oxidative deterioration (Moutounet and Escudier 2000).

Treating grapes by means of flash expansion (FE) technology also results in musts and juices enriched with all types of phenolic compounds. However, the concentration thereof decreases drastically throughout fermentation when a pressing treatment is applied after flash expansion. Wines obtained after fermenting musts treated using flash expansion have a higher concentration of flavonoids, catechins, anthocyanins and proanthocyanidins than control wines and slightly lower amounts of hydroxycinnamic acids. Keeping the grapes at a high temperature before FE treatment also increases the degree of phenolic compound extraction. On the other hand, high-temperature treatment also increases reactivity of phenolic compounds, and particularly conversion of anthocyanins into pigments showing more colors. FE increases the tannin-anthocyanin ratio and the formation of tannin-anthocyanin complexes favoring wine color stability (Morel-Salmi et al., 2006).

Flash vacuum expansion technology applied to lemon, orange, grapefruit and mandarin peels (heating with vapor followed by quickly going through a vacuum tank) allows obtaining essential oils by means of coupling a condenser and then separating them in a centrifuge. Obtained outputs were 2.41, 1.43, 0.64 and 0.73 k/ton of fruit for lemon, orange, mandarin and grapefruit, respectively. The obtained oils were enriched in limonene and other monoterpenes. The relative amounts of monoterpenes (linalool, alpha terpineol, beta citronellol, nerol, geraniol) and aldehydes (neral, geranial) were lower compared to the initial values initially obtained from the peel. The values of essential oils obtained from citrus peels by applying flash expansion are comparable to those obtained with FMC inline extractors when processing these citrus fruits. The obtained oils were rich in monoterpenes and correlatively depleted of volatile oxygenated constituents (Brat et al., 2001).

Another alternative technology with future prospects in the food, pharmaceutical and cosmetics industries is the use of high-intensity ultrasounds. Ultrasonic waves convert electric energy into mechanical vibration which in turn causes intense agitation of the molecule in the treated medium. Many specific ultrasound mechanisms are still unknown, but it has been demonstrated that most of them can be related to processes such as cavitation (formation of bubbles and the violent collapse thereof), heating (specific acoustic energy absorption), dynamic agitation, turbulence (micro-streams), and others. Large-amplitude waves (10 kHz-1 MHz) are generally the most suitable for applications such as cleaning, drilling, emulsification, welding, therapeutic uses, and chemical and biological applications. On the other hand, the low-amplitude waves are more effective for applications such as security systems, medical instrumentation, and material testing. In preparing foods, ultrasounds can be applied to cleaning, emulsifying, mixing, alcohol fermenting, extracting, cutting, drying, spraying, degassing and cell disruption (Koo Min et al., 2002).

Ultrasound technology is the result of the discovery of the piezoelectric effect by the Curies in 1880. Most ultrasound apparatus today are equipped with transducers that are based on this effect and convert electrical signals into mechanical signals, and vice versa. Most of the developments being made today focus on the design of this equipment and the design of electronic and computer circuits, taking into account understanding of the phenomenon of cavitation and its impact. Therefore, high-frequency alternating current can be converted into ultrasonic waves by means of an ultrasonic transducer (Mason, 1998). These waves can be amplified and applied by means of an ultrasound probe or an ultrasound bath. This probe can in turn be submerged in a liquid medium to be treated, or in the case of the bath, said bath is filled with the liquid to be treated. The antimicrobial effect of ultrasounds is due to cavitation, i.e., the extremely rapid formation and subsequent collapse of bubbles formed by ultrasonic waves in a medium (Earnshaw, 1998). Cavitation causes local changes in pressure and temperature, which causes break down of cell walls, disruption and thinning of cell membranes, and DNA damage by means of free radical production (Earnshaw et al., 1995; Sala et al., 1995).

There are different developments based on this technology. The combination of treatment with ultrasounds and high pressure leads to microbial inactivation. Ultrasounds do not have a strong lethal effect on microorganisms at ambient temperature and pressure (Raso et al., 1998; Pagan et al., 1999). High treatment intensities can cause microbial inactivation, but at the same time they cause adverse sensory changes in foods (Sala et al., 1995). A milder but effective treatment is called manosonication (MS). This treatment uses moderate doses of ultrasounds under slight pressure. In turn, manothermosonication (MTS) describes a manosonication process carried out at high temperatures (Hayden, 1991; Ordoñez et al., 1992; and Williams 1994). Raso et al. (Raso, Pagan et al., 1998) studied *Y. enterocolitica* inactivation by means of the combination of ultrasounds, pressure and heat. The lethal effect of ultrasounds (20 kHz, 150 Am) increased with the progressive increase in pressure until reaching an optimum value of 400 kPa. Levels of destruction of *B. subtilis* spores with MTS (20 kHz, 117 Am) followed a similar trend under increasing pressure, with maximum inactivation at a pressure of 500 kPa (Raso et al., 1998b). Pagan et al. (1999) also demonstrated *L. monocytogenes* inactivation by applying ultrasound (20 kHz, 117 Am). This inactivation increases drastically when pressure increases from ambient pressure to 200 kPa. However, the increase in the rate of inactivation became increasingly smaller over time, when pressure values went up from 200 to 400 kPa. The authors theorized that the higher lethal effect of ultrasounds with moderate pressure was due to the higher intensity of cavitation. It should be clarified that pressures applied during manosonication (for example, 200-600 kPa) are not within the lethal scope of pressures applied during high-pressure treatment (for example, 50-1000 MPa; Williams, 1994). Sala et al. (1995) demonstrated that the lethal effect of MTS treatments for bacterial cells, spores and fungi was 6.30-fold greater than thermal treatments that do not apply ultrasound and pressure, and they concluded that the combined effects of ultrasounds, pressure and heat were synergistic. Raso et al. (1998) and Pagan et al. (1999) also indicated that microbial inactivation increased when MS was combined with temperatures exceeding 50° C. However, the lethal effect of MS combined with heat gave only an additive, not synergistic, effect, which seems to be because both treatments act by means of two different and independent mechanisms, unlike the synergy between ultrasound and pressure.

Pagan et al. (1999) found that the effect of treating *Listeria monocytogenes* with ultrasound (20 kHz, 117 Am) under sub-lethal pressure levels (200 kPa) was not affected by a drop in pH from 7 to 4. Acidity conditions have a much greater effect on resistance of the organism to heat than on sensitivity thereof to ultrasounds. Similar findings were reported long before that by Kinsloe et al. (1954), who exposed bacterial and yeast cells to a sound field in saline suspensions of a different pH. The pH dropping from neutral to 4.0 did not affect mortality rates of *Pseudomonas aeruginosa* or *Saccharomyces cerevisiae* in ultrasounds. For *E. coli, Serratia marcescens* and *Micrococcus varians*, higher mortality rates were only observed when the treatment temperature was greater than 45° C. and treatment was combined with ultrasounds and lower values of pH (Kinsloe et al., 1954).

The combination of treatment with ultrasounds and antimicrobial agents is also effective. Arce-García et al. (2002) were able to reduce the intensity and duration of treatment with ultrasound necessary for inhibiting *Zygosaccharomyces rouxii* by 67% and 33%, respectively, by means of incorporating potassium sorbate, sodium benzoate or eugenol in the recovery medium. The authors suggest that the different modes of action of ultrasounds, mild heating (45° C.) and antimicrobial hurdles were responsible for the observed inhibition. Ahmed and Russell (1975) found that the combination of ultrasounds and hydrogen peroxide was much more lethal for *Bacillus* and *Clostridium* spores than any individually applied treatment. These authors postulated that the ultrasonic waves improve the lethal effect of hydrogen peroxide by means of an increase in cell permeability, increasing the rate of reaction between the hydrogen peroxide and cell components, and dispersion of cells aggregates, resulting in an increase in contact surface (Ross et al., 2003).

In summary, the description from the prior art of these technologies allows establishing the following.

Effect of ultrasounds: Although thermal treatment continues to be the most widely used pasteurization technique, there is growing interest in developing alternative preservation techniques causing minimal changes in organoleptic and nutritional properties. Non-thermal processing techniques that show potential include electric or magnetic fields, ionizing radiations, white light pulses, high hydrostatic pressures and use of ultrasounds. Ultrasounds have been identified as technology having enormous potential for meeting US Food and Drug Administration (FDA) requirements of a log reduction of 5 in survival of pertinent microorganisms that can be found in fruit juices. When high-power ultrasounds are propagated in a liquid, cavitation bubbles are formed due to intense changes in pressure. These microbubbles violently collapse in successive compression/vacuum cycles propagated in the sound wave, forming a cavitation series having intense destructive effects. There are several studies on the effects of ultrasounds in microbial inactivation of fruit juices.

Effect of the flash expansion process: during this treatment, the material to be treated is subjected to a mild heating process, such that the water contained inside the cells and structures increases in temperature, and when it is suddenly introduced in a high vacuum container, this temperature is enough to cause the immediate change from the liquid to the vapor state, causing the cells and structures to burst. The microorganisms can logically also be included during cell structure bursting, the material thereby being sterilized. This theoretical situation is distorted by the protective effect that certain plant structures have on the microorganism and prevent full effectiveness of this principle.

Hence the object of this invention; by introducing the impact of the series of ultrasonic bubbles at exactly the same time as the material is subjected to flash vacuum expansion, increasing the destructuring of the material and facilitating access of the vacuum to cell structures and the impact on the microorganisms.

The accumulated experience of the group of inventors based on different experiments that have been previously conducted (assays with the company Electricité de France (EDF), R&D with orange juice and ultrasound equipment that allowed pasteurizing juice with thermal treatments at a low temperature (50° C.) [Effects of ultrasonic treatments in orange juice processing. M. Valero, N. Recrosio, D. Saura, N. Muñoz, N. Martí, V. Lizama. Journal of Food Engineering 80 (2007) 509-516] but with very long processing times. Assays with flash expansion equipment on a semi-industrial level (1000 kg/hr), and with pilot glass equipment suitable for processing 10-20 kg/h) led to considering the designs and construction of equipment which will complement both actions. Equipment that can provide ultrasound treatment, while at the same time subjecting the material to be treated to continuous flash vacuum expansion, has been designed and constructed.

LITERATURE

Ashokkumar et al., (2008). "Modification of food ingredients by ultrasound to improve functionality: A preliminary study on a model system." Innovative Food Science & Emerging Technologies 9(2): 155-160.

Brat, P. (2001). "Application of flash-release, a new extraction procedure (juice, pulp, essential oil)." Fruitrop 85: 11-13.

Brat, et al., (2000). "Free Volatile Components of Passion Fruit Puree Obtained by Flash Vacuum-Expansion." Journal of Agricultural and Food Chemistry 48(12): 6210-6214.

Brat, et al., 2001. Essential Oil obtained by flash vacuum-expansion of peels, from lemon, sweet orange, mandarin and grapefruit. Fruits, vol 56, 395-402.

Bridgman, P. W. (1914). "The Coagulation of albumen by pressure." Journal of Biological Chemistry 19(4): 511-512.

Brillouet et al., 2001 "Preparation of Passion Fruit Puree by Flash Vacuum-Expansion" Journal of Food Science, 66 (4): 558-562.

Butz, et al., (2003). "Influence of ultra high pressure processing on fruit and vegetable products." Journal of Food Engineering 56(2-3): 233-236.

Certes, A. A. (1884). De l'action des hautes pressions sur les phénomènes de la putréfaction et sur la vitalité des microorganismes d'eau douce et d'eau de mer. Comptes Rendus, Gauthier-Villars.

Cogat Pierre Olivier et al. Aurore Development SA, et Centre de Cooperation Internationale en Recherché Agronomique pour le Development—Fr. "Procede de Fabrication d'un extrait d'agrumes reiche en pectine, et extrait obtenu par ce procede".

Earnshaw, R. (1996). "High pressure food processing." Nutrition & Food Science 96(2): 8-11.

Hayden, S. M. 1991. Apparatus and method for treatment of various liquid or slurry by ultrasonication in conjunction with heat and pressure. U.S. Pat. No. 5,026,564.

Hendrickx, et al., (1998). "Effects of high pressure on enzymes related to food quality." Trends in Food Science & Technology 9(5): 197-203.

Hite, B. H. (1899). The effect of pressure in the preservation of milk. A preliminary report, West Virginia University. Agricultural Experiment Station.

Institut Nationale de la Propriérté intellectuelle. Pub. 2 813010/reg. 0010646

Cogat Pierre Olivier. "Apparatus for processing hydrated biological materials." EP 0727948 (A1)—1996 Aug. 28. European Patent Office.

Knorr et al., (2004). "Applications and potential of ultrasonics in food processing." Trends in Food Science & Technology 15(5): 261-266.

Koo Min et al., (2002). "Physicochemical properties of sonicated mung bean, potato, and rice starches." Cereal Chemistry 79(5): 631-633.

Matser et al., (2004). "Advantages of high pressure sterilisation on quality of food products." Trends in Food Science and Technology 15(2): 79-85.

Merican, F. 2006 "Reduced—Pressure cooling method and installation for implementation same". Demande Internationalle de la Propriété intellectuelle, WO2006/024762A1.

Messens et al., (1997). "The use of high pressure to modify the functionality of food proteins." Trends in Food Science and Technology 8(4): 107-112.

Morel-Salmi et al., (2006). "Effect of Flash Release Treatment on Phenolic Extraction and Wine Composition." Journal of Agricultural and Food Chemistry 54(12): 4270-4276.

Moutounet, M. and J. L. Escudier (2000). "Pretreatment of grapes by flash release under vacuum. Effect on wine quality." Bulletin de l'O.I.V 73: 827-282.

Nadeau, Jean-Pierre. "System for cooling a heated Juice by Partial Low—Pressure evaporation. WO 02 096530 A2. Organisation Mondiale de la Propriété Intellectuelle"

Ordoñez Pereda, J. A.; Burgos González, J.; Raso Pueyo, J.; Lopez Buesa, P: Condon Uson, S. y Sala Trepat, F. J. (1992). "Procedimiento para la destrucciń de microorganismos y enzimas mediante la aplicación combinada de calor y ultrasonidos bajo presión: proceso MTS (Mano-Termo-Sonicación)". ES 2046944.

Pagan et al., (1999). "Resistance of Listeria monocytogenes to ultrasonic waves under pressure at sublethal (manosonication) and lethal (manothermosonication) temperatures." Food microbiology 16(2): 139-148.

Pierre Brat, Didier Ollé, Anne-Laure Gancel, Max Reynes and Jean-Marc Brillouet 2001 "Essential Oils obtained by flash vacuum—expansion of peels from lemons, sweet orange, mandarin and grapefruit" Fruits, vol, 56: 395-402

Raso et al., (1998). "Influence of Temperature and Pressure on the Lethality of Ultrasound." Applied and Environmental Microbiology. 64(2): 465-471.

Raso et al., (1998b). "Inactivation of Bacillus subtilis spores by combining ultrasonic waves under pressure and mild heat treatment." Journal of Applied Microbiology 85(5): 849-854.

Ross et al., (2003). "Combining nonthermal technologies to control foodborne microorganisms." International Journal of Food Microbiology 89(2-3): 125-138.

Sala et al., (1995). "Effect of heat and ultrasound on microorganisms and enzymes." New Methods of Food Preservation. G. W. Gould. London, Springer.

Señorans et al., (2003). "New Trends in Food Processing." Critical Reviews in Food Science and Nutrition 43(5): 507-526.

Urrutia-Benet et al., (2004). "High pressure-low temperature processing. Suggested definitions and terminology." Innovative Food Science and Emerging Technologies 5(4): 413-427.

Williams, A. (1994). "New technologies in food processing: Part II." Nutrition and Food Science 94(1): 20-23.

SUMMARY OF THE INVENTION

The apparatus object of the invention is obtained by coupling flash expansion equipment of an ultrasound treatment system with a speaker- or horn-like probe designed specifically so that the material to be treated circulates in the interior thereof (or on the surface thereof) at exactly the same time the product is subjected to flash vacuum expansion. The operating principle of the apparatus is shown in FIG. 1. The result of this coupling is a new method in which the effects of cavitation caused by ultrasounds and flash vacuum expansion are advantageously combined. Therefore at the same time as the impact of cavitation bubbles takes place, with the concomitant effects of extremely high pressures due to impact of the bubble wavefront and subsequently due to suction as the sound bubble goes through the material, combined with the high temperature generated by such impacts, biological structures undergo destabilization which is gradually accentuated by stresses because the water contained in said structures is greatly expanded on the way to being gassed at the treatment temperature. The biological structures of the material are therefore simultaneously subjected to extremely high impact and suction pressures, extremely high temperatures due to impact and bursts due to the increase in the volume of water contained in the medium when subjected to a vacuum. The synergistic effect of the assembly is what makes the system so effective.

The invention consists of an apparatus capable of advantageously and simultaneously combining the effects of flash vacuum expansion and ultrasounds. The apparatus is therefore capable of causing the water content in the treated material to expand abruptly in a vacuum and ultrasound cavitation bubbles to impact against it at the same time. At the same time, the material to be treated is dispersed in uniform droplets of about 90 microns in diameter, whereby facilitating the effect of both the flash vacuum and ultrasound bubbles. The innovation therefore results from the assembly of known elements which allows starting up objectively new and improved equipment. The features of the equipment are described below.

Figure 2:
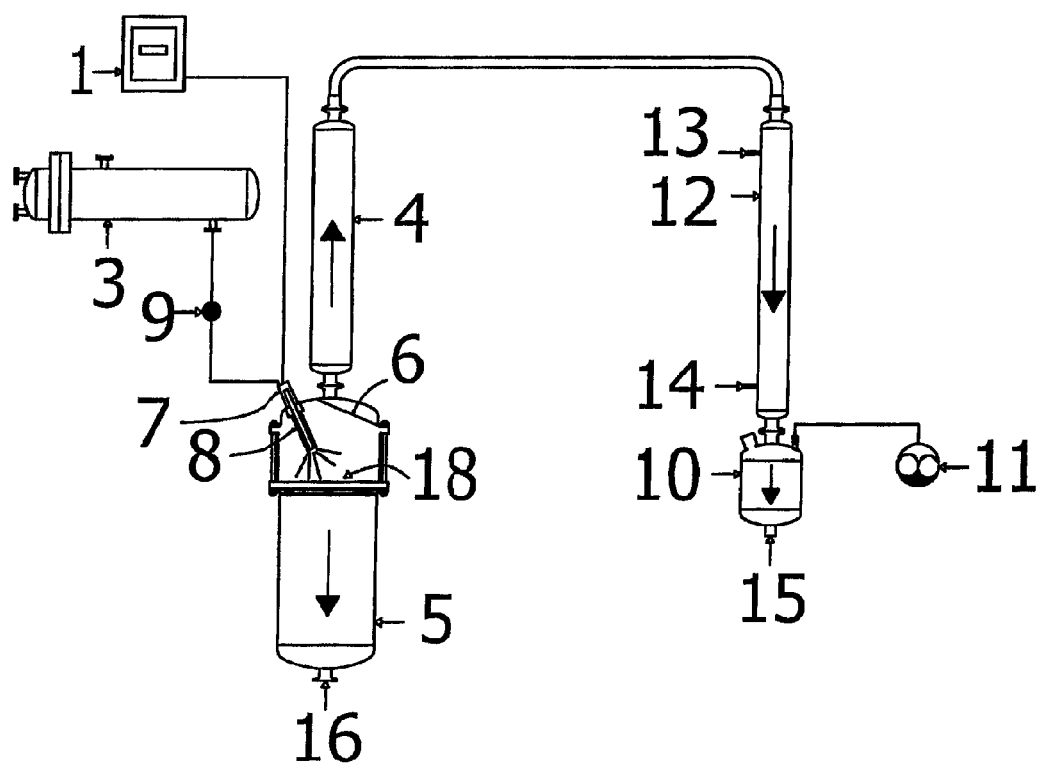
Figure 3:
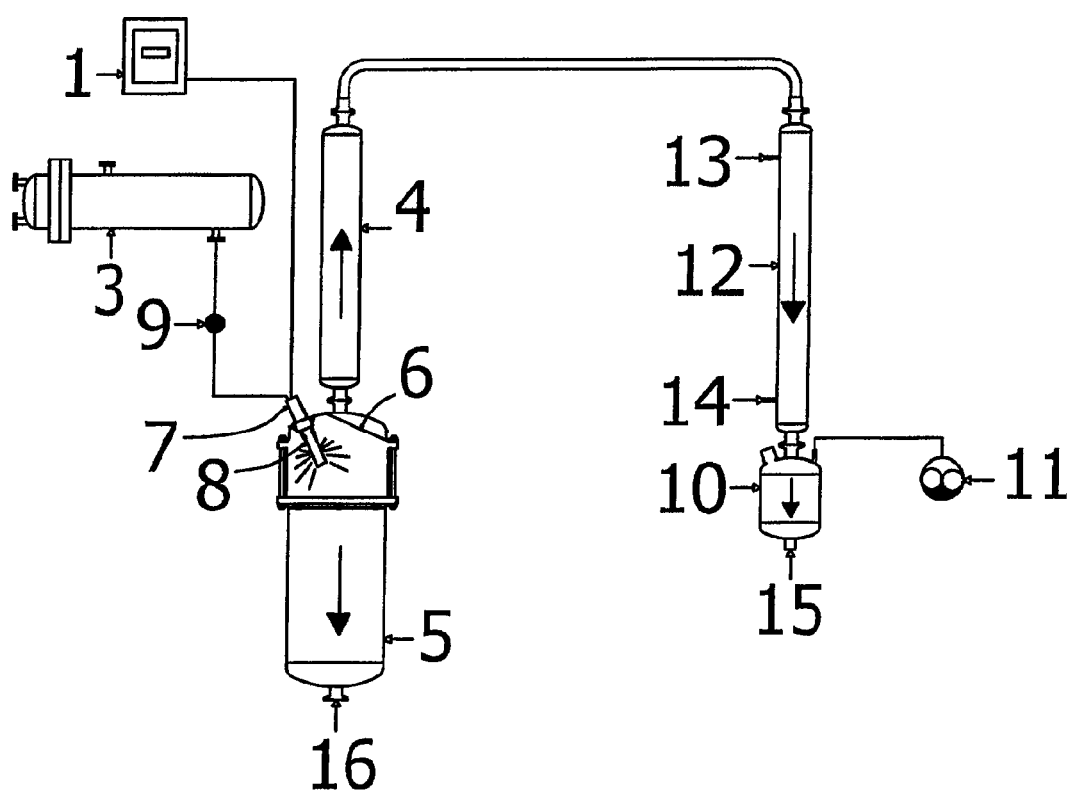
Figure 4:
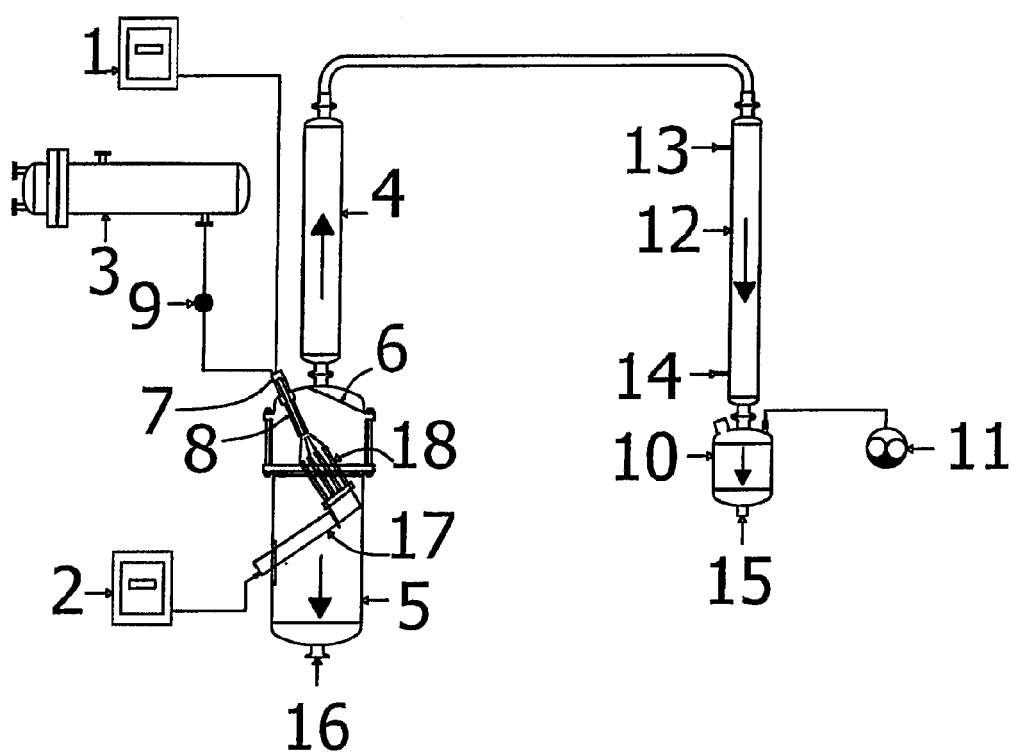

The invention was initially developed in the form of three apparatus. Diagrams of the apparatus and the possible assembly thereof are shown in FIGS. 2, 3 and 4. The three apparatus have a common part which corresponds to the following description. FIG. 2 shows an apparatus in which the effect described in this patent could be observed. This does not mean that it is the only alternative, or that including it in the present patent specification restricts the applications of this invention.

The equipment consists of a heat exchanger (reference number 3 in FIGS. 2, 3 and 4) responsible for heating the material to be treated. This exchanger is coupled by means of a manual pneumatic valve to a cylindrical stainless steel reactor equipped with a thermostat (reference number 5 in FIGS. 2, 3 and 4), fed at normal pressure (by means of a pump, reference number 9 in FIGS. 2, 3 and 4), acting like a chamber where a vacuum is generated by means of a refrigerated vacuum pump (reference number 11 in FIGS. 2, 3 and 4). Condensed vapors are collected in a droplet separator (reference number 4 in FIGS. 2, 3 and 4). The apparatus is equipped with a baffle element (reference number 6 in FIGS. 2, 3 and 4) that prevents the bubbles from entering the droplet separator. The aromatic liquors generated by the flash evaporation of water and volatile substances are collected in a container for condensates (reference number 10 in FIGS. 2, 3 and 4) after going through a coil exchanger (reference number 12 in FIGS. 2, 3 and 4) cooled with glycol water (with an inlet and outlet with reference numbers 13 and 14 in FIGS. 2, 3 and 4). The equipment comprises two discharge systems, the discharge system of the vacuum reactor (reference number 16 in FIGS. 2, 3 and 4), through which the treated material is obtained, and the discharge system of the container for condensates, through which condensed gases are collected (reference number 15 in FIGS. 2, 3 and 4). The droplet separator and coil are connected by means of an inclined connector. Up to this point, the design is common in the three apparatus. The difference is in the manner of applying ultrasounds. The two remaining apparatus are also described.

In apparatus A (FIG. 2), the material to be treated goes through the interior of a probe (reference number 8 in FIG. 2) where it is subjected to ultrasounds. The material is also subjected to a vacuum inside the probe. The output of the ultrasound probe goes towards the interior of the vacuum reactor where the sample ends up exiting in the form of dispersed droplets (diameter of 90 microns) in the form of cloud which burst when the vacuum is completed (operation of this equipment is shown schematically in FIG. 1). The ultrasound equipment is complemented by the transducer (reference number 7 in FIG. 2) and the ultrasound generator (reference number 1 in FIG. 2).

In apparatus B (FIG. 3), the material to be treated is introduced inside the vacuum reactor such that it is deposited in the form of a thin film on the planar surfaces of the ultrasound-generating probe. The probe is designed such that the ultrasounds generate a fine cloud of microdroplets (diameter of 90 microns) from the film of the material to be treated that is fed thereto. In this equipment, the cavitation bubbles impact against the material to be treated at the same time the microdroplets are generated and the material comes into contact with the flash vacuum. The ultrasound equipment is complemented by the transducer (reference number 7 in FIG. 2) and the ultrasound generator (reference number 1 in FIG. 2).

In apparatus C (FIG. 4), the material to be treated goes through the interior of a probe (8 in FIG. 4), just as in the case of the design of apparatus A. The difference is that in this apparatus, the cloud of microdroplets impacts against a second probe, formed by a group of planar ultrasound probes (18 in FIG. 4), such that the material is subjected to a new cavitation treatment by means of ultrasounds in the device formed by the group of probes placed exactly opposite the outlet of the first probe (8 in FIG. 4) in the presence of the vacuum in the reactor. The ultrasound equipment is complemented by transducers (7 for the first probe and 17 for the second probe in FIG. 4) and ultrasound generators (1 for the first probe and 2 for the second probe in FIG. 4).

BRIEF DESCRIPTION OF THE DRAWINGS

FIG. 1 is a perspective view of an apparatus according to the present invention.

FIG. 2 depicts apparatus A as described herein.

FIG. 3 depicts apparatus B as described herein.

FIG. 4 depicts apparatus C as described herein.

DETAILED DESCRIPTION OF THE INVENTION

FIG. 1 shows the principle on which the new system is based, in which the application of ultrasounds at the same time the vacuum is triggered synergistically multiplies the effects on the material.

FIG. 2 shows an embodiment of the invention, apparatus A, in which the ultrasound treatment takes place inside the probe where the vacuum is also generated. The material is introduced in the vacuum reactor through the probe.

FIG. 3 shows an embodiment of the invention, i.e., apparatus B, in which the ultrasound treatment takes place on the surface of the probe where the vacuum is also generated. The material is introduced in the vacuum reactor by means of a side feed on planar surfaces of the probe.

FIG. 4 shows the equipment, in which the two complementary ultrasound probe systems are combined.

The present invention is additionally illustrated by means of the following examples, which do not intend to limit the scope thereof.

Apparatus B was used in all the examples according to the design described in FIG. 3 as it is between apparatus A and apparatus C. The microorganism count was done in all the examples according to the following protocol. Active growth cultures were prepared in tryptone soy broth (TSB) for *E. coli* CECT 515 and in potato dextrose broth (PDB) for *S. cerevisiae* RJ-11 Rouge Jeune, incubated for 18-42 hours at 37° C. and 25° C., respectively. The cultures were centrifuged at 10000×g for 10 minutes at 4° C. The sediments were resuspended and diluted in phosphate buffer pH 5.7 and citrate buffer pH 3.2, depending on whether they are bacteria or yeasts, until obtaining a final concentration of $10^6$ colony forming units (CFU)/ml. Sabouraud dextrose chloramphenicol agar (SDCA) plates and eosin methylene blue (EMB) agar plates were used for counting the viable microorganisms on the surface before and after processing.

Example 1

In this example, a fluid containing an initial yeast population of the *Saccharomyces cerevisiae* species is processed using to that end the apparatus described in FIG. 3.

The characteristics of the fluid are: citric acid/sodium citrate buffer at pH 3.2, prepared using 43.7 ml of a 0.1 M citric acid solution and 6.3 ml of a 0.1 M sodium citrate solution, diluted in a total of 100 ml. The initial microbial inoculum population was 106 CFU/ml.

A sample having a volume of 5.120 kg heated at 50° C. in the heat exchanger (3 in FIG. 3) was processed under these conditions. This sample was then introduced in the reactor (reference number 5 in FIG. 3) through a feed system oriented such that the fluid slides over the surface of the ultrasound probe (reference number 8 in FIG. 3), causing atomization thereof. This atomization takes place due to the impact of generated ultrasounds on the surface of the probe at a frequency of 20 kHz and at a power of 750 Watts. At the same time, the liquid is made to flow in the reactor under constant volume conditions and vacuum conditions of up to 0.07 bar. The vacuum is generated by means of the vacuum pump (reference number 11 in FIG. 3).

A log reduction>5 Log CFU/ml is achieved under these conditions, implying complete pasteurization.

Example 2

In this example, a fluid containing an initial enterobacteria population of the *Escherichia coli* species is processed using to that end the equipment described in FIG. 3.

The characteristics of the fluid are: phosphoric acid/sodium phosphate buffer at pH 5.7, prepared using 93.5 ml of a 0.2 M monobasic sodium phosphate solution and 6.5 ml of a 0.2 M dibasic sodium phosphate solution, diluted in a total of 200 ml. The initial microbial inoculum population was 106 CFU/ml.

A sample having a volume of 4.930 kg heated at 50° C. in the heat exchanger (reference number 3 in FIG. 3) was processed under these conditions. This sample was then introduced in the reactor (reference number 5 in FIG. 3) through a feed system oriented such that the fluid slides over the surface of the ultrasound probe (reference number 8 in FIG. 3), causing atomization thereof. This atomization takes place due to the impact of generated ultrasounds on the surface of the probe at a frequency of 20 kHz and at a power of 750 Watts. At the same time, the liquid is made to flow in the reactor under constant volume conditions and vacuum conditions of 0.05 bar. The vacuum is generated by means of the vacuum pump (reference number 11 in FIG. 3).

A log reduction of 5 Log CFU/ml is also achieved under these conditions, implying complete pasteurization.

The invention claimed is:

1. An apparatus for treating biological or chemical materials, comprising:
    (a) a heat exchanger in which the materials are subjected to preheating to create a preheated material;
    (b) a vacuum reactor into which the preheated material is fed, and in which a portion of water contained in the material is vaporized, the heat exchanger and vacuum reactor also being connected such that a pressure difference between the vacuum reactor and heat exchanger is maintained;
    (c) an ultrasound probe acting on the material inside the vacuum reactor simultaneously to the instant in which the material is introduced into said vacuum reactor;
    (d) the vacuum reactor connected to a condensation system, the condensation system connected to a vacuum source.

2. The apparatus according to claim 1, wherein the material circulates through said ultrasound probe, the material thereby being fed into the vacuum reactor.

3. The apparatus according to claim 2, further comprising a second ultrasound probe which, when placed opposite the first ultrasound probe inside the vacuum reactor, acts on an outgoing stream by applying a second ultrasound treatment on the material.

4. The apparatus according to claim 3, further comprising a recovery system recovering the treated materials and condensed vapors.

5. The apparatus according to claim 2, further comprising a system for recovering the treated materials and condensed vapors.

6. The apparatus according to claim 2, further comprising a recovery system recovering the treated materials and condensed vapors.

7. The apparatus according to claim 1, wherein a feedstream of the material strikes a surfaces of said ultrasound probe, thereby being fed into the vacuum reactor.

8. The apparatus according to claim 7, further comprising a recovery system recovering the treated materials and condensed vapors.

9. The apparatus according to claim 1 further comprising a condensation system formed by:
    (a) a cylinder connected to an upper part of the vacuum reactor and forming a droplet separator, having a sufficient size to preventing the material from following the vapors to the vacuum pump;
    (b) a cooling exchanger through which the vapors pass, the cooling exchanger cooling the vapors to the condensation temperature thereof;
    (c) a container for condensates where condensed vapors are collected and separated from a gas stream into the vacuum pump.

10. A method of destroying microorganisms in a biological or chemical material comprising:
    heating the material via a heat exchanger;
    feeding the material into a vacuum reactor after said heading step;
    vaporizing a portion of water contained in the material in the vacuum reactor; and
    treating the material inside with an ultrasound probe.

11. The method of claim 10 wherein the material is pasteurized and sterilized by the method.

12. The method of claim 10 wherein said treating step further comprises treating an outgoing stream of the material with a second ultrasound probe.

13. The method of claim 12 wherein the material is pasteurized and sterilized by the method.

14. The method of claim 10 further comprising striking a surface of said ultrasound probe with a feedstream of the material.

15. The method of claim 14 wherein the material is pasteurized and sterilized by the method.

16. The method of claim 10 wherein said treating step occurs during said feeding step such that the material is fed through said ultrasound probe.

17. The method of claim 16 wherein the material is pasteurized and sterilized by the method.

* * * * *